United States Patent [19]

Carlo et al.

[11] 4,287,173

[45] Sep. 1, 1981

[54] VACCINE FOR DENTAL CARIES

[75] Inventors: Dennis J. Carlo, Middlesex; Jesse J. Jackson, Marlboro; Thomas H. Stoudt, Westfield, all of N.J.

[73] Assignee: Merck & Co., Inc., Rahway, N.J.

[21] Appl. No.: 77,971

[22] Filed: Sep. 24, 1979

[51] Int. Cl.³ .................. A61K 7/16; A61K 39/00; A61K 31/70

[52] U.S. Cl. ...................... 424/49; 424/88; 424/180; 424/92

[58] Field of Search ............... 536/1; 424/92, 180, 424/49, 88

[56] References Cited

U.S. PATENT DOCUMENTS

| | | | |
|---|---|---|---|
| 3,029,187 | 4/1962 | Steinhardt et al. | 107/60 |
| 3,312,594 | 4/1967 | Norman | 167/82 |

FOREIGN PATENT DOCUMENTS 2404 6/1979 European Pat. Off. .

OTHER PUBLICATIONS

McGhee, J., et al., J. Immun., vol. 114, 300 (1975).
Evans, R., et al., Injection and Immunity, vol. 12, 293 (1975).
Emmings, F., et al., Impaction and Immunity vol. 12, 281 (1975).
Russell, M., et al., Immunology, vol. 30, 619 (1976).
Taubman, M., et al., J. Immun, vol. 118, 710 (1977).
Michalek, S., et al., Injection and Immunity, vol. 19, 217 (1978).
Guggenheim, B., et al., Secretory Immunity and Injection, Proceedings of International Symposium on the Secretory Immune System and Caries Immunity, 1978, pp. 293-299, Plenum Press, New York and London.
Borgono, J., et al., Proceeding of Society for Experimental Biology and Medicine, vol. 157, 148-154 (1978).
Austrian, R., New Approaches for Inducing Natural Immunity to Pyogenic Organism, Mar. 21-23, 1973, Florida, pp. 39-44.
Keyes, J. Dental Res., vol. 37, 1088 (1958).

*Primary Examiner*—Delbert R. Phillips
*Assistant Examiner*—Blondel Hazel
*Attorney, Agent, or Firm*—Donald J. Perrella; Theresa Y. Cheng; Hesna J. Pfeiffer

[57] ABSTRACT

A vaccine against dental caries is prepared from capsular polysaccharides (one or more strains), of *Streptococcus pneumoniae*.

8 Claims, No Drawings

VACCINE FOR DENTAL CARIES

BACKGROUND OF THE INVENTION

Dental caries (cavities) is an infectious disease ubiguitous in civilized populations. Its treatment costs billions of dollars per year and entails considerable discomfort. Caries—the destruction of enamel, dentin, or cementum—has a multifactorial etiology which includes host susceptibility, diet containing fermentable carbohydrates and cariogenic microorganisms. In recent years, certain oral streptococci, notably *Streptococus mutans* have been associated with caries in man and in experimental animals such as the monkey, rat and the hamster. *S. mutans* produces the enzyme, glucosyltransferase, which in the presence of sucrose forms high molecular weight dextran-like glucose polymers called glucans or mutans. Studies have suggested the importance of this glucan in the virulence of this organism since its synthesis facilitates microbial adherence to hard surfaces and also contributes to dental plaque formation. In addition, microbial fermentation of glucose and fructose moieties of sucrose results in production of lactic acid, which is involved in demineralization of the tooth surface, thus initiating the carious lesion.

Treatment of experimental animals with antibiotics has shown very significant decreases in the incidence of cariogenic lesions. However, the indigenous bacteria found in the oral cavity and other portions of the alimentary canal play a major role in preventing certain other bacterial diseases through effects collectively referred to as bacterial antagonism. Thus, when broad-spectrum antibiotics, such as tetracyclines, are given in large doses for many days, growth of most of the bacteria that normally thrive in the oral cavity and intestinal tract is suppressed. As a result, antibiotic-resistant strains of potentially pathogenic organisms, normally held in check by antagonistic action, multiply freely and occasionally give rise to a serious, and often fatal, disease, such as acute staphylococcal enteritis. Therefore, the use of general antibiotics does not appear to be a factor for consideration in any attempt to induce protection against dental caries.

OBJECTS OF THE INVENTION

It is an object of the present invention to provide a subunit vaccine for dental caries. Another object is to provide a subunit vaccine derived from *Streptococcus pneumoniae* for dental caries. Yet another object is to provide compositions for administering a vaccine against dental caries. A further object is to provide a method for preventing dental caries. These and other objects of the present invention will be apparent from the following description.

SUMMARY OF THE INVENTION

A vaccine against dental caries is prepared from the capsular polysaccharides of at least one of *S. pneumoniae* types 4, 12 or 19. Local immunization is preferred over a remote site vaccination.

DETAILED DESCRIPTION

The present invention relates to a vaccine against dental caries and, more particularly, to a vaccine utilizing capsular polysaccharides from *S. pneumoniae*.

The dental caries vaccine of the present invention is based on the discovery that antibody to capsular polysaccharides of *S. pneumoniae* types 4, 12 and 19 cross-react with *S. mutans* in vitro. The preparation of the foregoing capsular polysaccharides of *S. pneumoniae* is disclosed in European patent specification published 13 June 1979 under No. 2404, the disclosure of which is hereby incorporated by reference.

The capsular polysaccharides of *S. pneumoniae* types 4, 12 and 19 are effective individually or in combination as a prophylactic agent to reduce dental caries in a susceptible mammalian species, e.g. rats. These capsular polysaccharides may be administered locally in the gum or buccal region either topically or by injection or at a remote site by injection. Local administration, however, is preferred. The capsular polysaccharide or polysaccharides are administered in a dosage level effective to reduce the incidence of dental caries. This level typically is from about 1 to about 100 $\mu$g per type of capsular polysaccharide. The capsular polysaccharides may be administered singly or in combinations of any two of the 3 types, or all 3 types combined. Aqueous formulations are preferred. When more than one capsular polysaccharide is to be employed, the individual capsular polysaccharides may be administered sequentially or simultaneously in a composition containing 2 or 3 of the capsular polysaccharides.

For topical administration the polysaccharide may be applied in the form of aqeuous solutions or ointments. The aqueous solutions comprise the capsular polysaccharide or polysaccharides in a physiologically acceptable aqueous liquid such as, for example, saline, phosphate buffered saline, or water. The ointments comprise the capsular polysaccharide or polysaccharides in adhesive preparations such as, for example, those described in U.S. Pat. Nos. 3,029,187; 3,029,188 or 3,312,594, the disclosure of which are hereby incorporated by reference.

The following protocol is employed in evaluating the effectiveness of capsular polysaccharides from *S. pneumoniae* in preventing dental caries. Weanling Sprague-Dawley (CD-1) femal rats (18 days old) obtained from Charles River are housed (one animal/cage) in screen bottom caging. The average weight per rat is 30 grams. Upon arrival, 18-day old rats are immediately placed on a high sucrose diet and glass distilled water. During the first week, rats are given water via a water dish but are subsequently watered via an automatic watering system or watering bottles.

| Diet (Stored at 4° C.) | | |
|---|---|---|
| | Ingredients | Percent by Weight |
| a. | 6X Confectioners sugar | 56 |
| b. | Skim milk powder | 28 |
| c. | Whole wheat flour | 6 |
| d. | Dried Brewers Yeast | 4 |
| e. | Whole liver powder | 1 |
| f. | Powdered alfalfa herb | 3 |
| g. | Sodium chloride | 2 |

The dental caries infection is initiated in the following way: A lyophilized culture of *S. mutans* is opened, suspended in 15 ml of Fluid Thioglycollate medium containing 0.5% sucrose and incubated overnight at 37° C. as a seed culture. The entire seed culture is inoculated into 250–500 ml of liquid thioglycollate medium plus 0.5% sucrose and incubated at 37° C. for 18 hours. After confirming culture purity microscopically, this suspension is used for the initial infection and subculturing.

Groups of 20 rats are orally infected with *S. mutans* (cariogenic organisms) by swabbing each rat with a cotton tip applicator soaked in an overnight (18 hour) culture. The animals are infected by oral swabbing for three consecutive days (days 19, 20 and 21). Five to 7 ml of an 18-hour culture is placed in their drinking water for 2-3 additional days (used but found not essential). The animals are injected with the vaccine (pneumococcal polysaccharide type 4, 12, or 19) on days 19, 20 and 21; each rat receives three injections consisting of 1.0 µg of each polysaccharide in 0.1 ml of saline (0.85%). Water solutions are also effective. Injections are given subcutaneously in the submandibular region. Booster injections are preferred at weekly intervals beginning at day 28.

The rats are sacrificed 45 days after the last day of injection (68 days after birth). The animals are decapitated and individual heads are placed in beakers covered with porous aluminum foil. They are autoclaved for 15 minutes and the lower jaws are stained and prepared for scoring, they are scored by the method of Keyes, J, Dental Res. 37, 1088 (1958).

The following examples illustrate the present invention without, however, limiting the same thereto.

EXAMPLE 1

*S. pneumoniae* type 12 capsular polysaccharide is used according to the foregoing protocol both alone in aqueous solution and also complexed with an equal weight of lipid A (isolated from *S. minnesota* Re 595. The complex is formed by solubilizing lipid A in triethanolamine and this is added to an equal volume of aqueous solution of the polysaccharide. The ethanolamine is then evaporated and the preparation is lyophilized. Groups of 18-day old weanling Sprague-Dawley rats are used for vaccination. Both test groups are vaccinated on days 19, 20 and 21; additionally booster vaccinations of the vaccines are given on days 28, 35 and 42. The diet of the rats is as specified in the protocol. The scoring results are given in the following table.

by the results, enamel damage is reduced in pneumococcal polysaccharide type 12 vaccinates.

In the way of explanation under Enamel, T STATS.—the numbers in parenthesis are degrees of freedom and the other numbers are the actual T values. $\overline{X}$ represents the means of the scores and SEM is the standard error of the mean. Column E represents enamel caries; scores are relative to the 100% value given to the control. $D_S$, $D_M$, and $D_X$ refer to depth of the carious lesion in the dentin. S is slight, M is moderate, and X is extensive. $\overline{X}D$ is the means of the dentin scores. $\overline{X}$ is absolute value of caries in dentin while the number in parenthesis is % inhibition of caries. These reductions are highly significant statistically.

EXAMPLE 2

Following the above-described protocol, the following experiment is conducted.

| Injection Site | Antigen | Protection vs. *Str. mutans* Challenge | |
|---|---|---|---|
| 1 Local | Pn-12 Polysaccharide | + | |
| 2 Remote | Pn-12 Polysaccharide | — | |
| 3 Local | Whole Cell Pn-12 | + | ≈ Pn-12 Polysaccharide |
| 4 Local | Pn-12, 4 and 19 | + | > Pn-12 Polysaccharide (Local) |
| 5 Local | Pn-4 Polysaccharide | — | |
| 6 Remote | Pn-4 Pooysaccharide | — | |
| 7 Local | Pn-4 Whole Cell | + | > Pn-12 Polysaccharide, Whole Cell Pn-12 > Pn-12, 4 and 19 (1:1:1) |
| 8 Local | Pn-19 Polysaccharide | + | ≈ Pn-12 Polysaccharide |
| 9 Local | Pn-34-3 Polysaccharide | — | |

Maximum reduction in this experiment was 51% *Streptococcus mutans* (LM-7, MB3715) challenge.

All antigens are inoculated to give a final dosage of 1.0 µg/injection except for whole cell preparations. Whole cell preparations are ~$10^7$ to $10^8$ cells/ml.

All of the above antigens are injected in 0.1 ml volumes on days 19, 20 and 21. Boosters are given twice at 7 day intervals, the first at day 28.

| Antigens | Dose µg | No. Inj. | Enamel T STATS. | Enamel $\overline{X}$ SEM | $D_S$ T STATS. | $D_S$ $\overline{X}$ SEM | $D_M$ T STATS. | $D_M$ $\overline{X}$ SEM | $D_X$ T STATS. | $D_X$ $\overline{X}$ SEM |
|---|---|---|---|---|---|---|---|---|---|---|
| A Lipid A | 1 | 3 | — | 22.95 ±2.02 | — | 15.11 ±2.04 | — | 13.26 ±2.03 | — | 10.74 ±2.03 |
| B Pn-12* Polysaccharide | 1 | 3 | 2.70 (37) | 16.40 ±1.38 | 3.05 | 8.05 ±1.16 | 3.59 | 5.21 ±0.95 | 3.16 | 3.95 ±0.82 |
| C Pn-12* Polysaccharide + Lipid A | 1+1 | 3+3 | 2.20 (37) | 17.20 ±1.67 | 3.31 | 7.30 ±1.24 | 3.29 | 5.65 ±1.17 | 3.32 | 3.40 ±0.97 |

| Antigens | Dose µg | No. Inj. | E % | $D_S$ % | $D_M$ | $D_X$ | $\overline{X}$% | $\overline{X}D$ |
|---|---|---|---|---|---|---|---|---|
| A Lipid A | 1 | 3 | 100 | 100 | 100 | 100 | 100 | (0) |
| B Pn-12* Polysaccharide | 1 | 3 | 71.5 | 53.3 | 39.3 | 36.8 | 43.1 | (56.9) |
| C Pn-12* Polysaccharide + Lipid A | 1+1 | 3+3 | 75.0 | 48.3 | 42.6 | 31.7 | 40.9 | (59.1) |

*PN-12 is *S. pneumoniae* capsular polysaccharide type 12.

In this example, lipid A vaccinations are performed to obtain a placebo control. The pneumococcal polysaccharide is injected alone and in combination with lipid A to demonstrate that lipid A does not effect caries scores. For example, the result of pneumococal polysaccharide type 12 alone is found to give a caries reduction calculated to be 56.9% of the dentine, while the pneumococcal polysaccharide plus lipid A is 59.1% reduction. This difference is insignificant. Also, as can be seen Pneumococcal type 12 polysaccharide produces the normal protection observed in Example 2 when given locally (submandibular). On the other hand, remote site (rear leg) vaccination gives no protection at the same dose. Normally, the polysaccharide response in man is greater than that in animals; because of this, a whole cell pneumococcal type 12 vaccine is tested.

Results are comparable to that obtained with type 12 capsular polysaccharide. In the case of pneumococcal type 4, however, only the whole cell resulted in protection. In the case of pneumococcal type 19, the polysaccharide protected. Pneumococcal polysaccharide type 34 is run as a polysaccharide placebo control and it has no effect on caries scores. The combination of pneumococcal polysaccharides types 4, 12 and 19 produces better protection than either one alone.

EXAMPLE 3

An oral adhesive preparation is made following the procedure of Example 1 of U.S. Pat. No. 3,029,188. Fifty μg of S. pneumoniae capsular polysaccharide type 12 is added to 1 gram of the oral adhesive preparation and blended until homogeneous. The resulting preparation is then applied to the upper and lower gums of a group of rats. Similar preparations are made by substituting types 4 and 19 for 12.

EXAMPLE 4

The procedure of Example 3 is repeated except that the 50 μg of type 12 capsular polysaccharide are added in the form of an aqueous solution containing type 12 capsular polysaccharide in a concentration of 1 mg/ml.

EXAMPLE 5

The procedures of Examples 3 and 4 are repeated except that bivalent or trivalent compositions are prepared containing 50 μg of each of the following S. pneumoniae capsular polysaccharide types:
(a) types 4 and 12
(b) types 4 and 19
(c) types 12 and 19
(d) types 4, 12 and 19.

What is claimed is:

1. A method of reducing the incidence of dental caries in a susceptible mammalian species comprising administering an effective amount of a capsular polysaccharide of S. pneumoniae type 4, 12 or 19.

2. A method according to claim 1 wherein the capsular polysaccharide is administered locally.

3. A method according to claim 2 wherein the capsular polysaccharide is administered topically.

4. A method according to claim 1 wherein at least two capsular polysaccharides are administered substantially simultaneously.

5. A method according to claim 1 wherein all three capsular polysaccharides are administered substantially simultaneously.

6. An anti-caries composition consisting essentially of at least two capsular polysaccharides of S. pneumoniae types 4, 12 or 19 in an anti-caries effective amount in a physiologically acceptable medium, the total amount of capsular polysaccharide in the anti-caries composition not exceeding about 100μg per type and a pharmaceutically acceptable topical carrier.

7. A composition according to claim 6 wherein the carrier is an ointment suitable for typical administration.

8. A composition consisting of the three capsular polysaccharide of S. pneumoniae types 4, 12 and 19 according to claim 6.

* * * * *